United States Patent [19]
Giolando

[11] Patent Number: 5,817,847
[45] Date of Patent: Oct. 6, 1998

[54] METHOD OF PRODUCING ORGANO INDIUM CHLORIDES

[75] Inventor: Dean M. Giolando, Toledo, Ohio

[73] Assignee: Libbey-Owens-Ford Co., Toledo, Ohio

[21] Appl. No.: 871,934

[22] Filed: Jun. 10, 1997

Related U.S. Application Data

[63] Continuation of Ser. No. 705,913, Aug. 29, 1996, Pat. No. 5,663,390.

[51] Int. Cl.$^6$ ....................................................... C07F 5/00
[52] U.S. Cl. .................................................................. 556/1
[58] Field of Search ...................................................... 556/1

[56] References Cited

U.S. PATENT DOCUMENTS 3,082,232  3/1963  Nowlin et al. ........................... 260/448

OTHER PUBLICATIONS

Handbook of Chemistry and Physics, 63rd Edition, CRC Press, Inc., p. B–105, 1982–1983.

*Primary Examiner*—Porfirio Nazario-Gonzalez
*Attorney, Agent, or Firm*—Marshall & Mehlhorn

[57] ABSTRACT

A method for producing organo metal chlorides directly from molten metal. The organo metal chlorides are formed by contacting an organo chloride directly with a metal melt. The preferred method includes the use of indium as the metal and methyl chloride as the organo chloride. The direct contact of the methyl chloride with the indium metal results in the production of dimethyl indium chloride or methyl indium dichloride depending on the contacting time and efficiency of the process. The resulting products are suitable for use as a precursor gas for chemical vapor deposition processes. Additionally, activator compounds such as oxides or halides are optionally added to the metal melt to enhance the reaction rate.

15 Claims, 2 Drawing Sheets

METHOD OF PRODUCING ORGANO INDIUM CHLORIDES

This application is a continuation of application Ser. No. 08/705,913, filed Aug. 29, 1996, now U.S. Pat. No. 5,663,390.

BACKGROUND OF THE INVENTION

1. Field of the Invention

This invention relates to a method for producing organo metal chlorides directly from a molten metal. More particularly, this invention relates to a method for producing organo indium chlorides by contacting an organo chloride with an indium metal melt to form an organo indium chloride. The direct contact of the organo chloride with the indium metal melt results in the production of either diorgano indium chloride or organo indium dichloride depending on the contacting time and efficiency of the process. Additionally, activator compounds are optionally added to the metal melt to enhance the reaction rate. Gallium metal is also suitable for use with the inventive method for forming organo gallium chlorides.

2. Summary of Related Art

Organo metal chlorides are organo-metallic compounds that dissociate under pyrolytic reaction conditions. The dissociation permits the use of the compounds as a source for metal in chemical vapor deposition processes. Thus, the organo metal chlorides, particularly organo indium chlorides, are desirable for use as precursors in chemical vapor deposition processes for laying down metal oxide or doped metal oxide films or coatings onto substrates. Additionally, the deposition rates of indium oxide, or doped indium oxides, through the use of organo indium chlorides as precursors, are higher than other conventional indium precursors. The higher deposition rates are desirable for applying coatings on substrates, such as a continuous glass ribbon in a float glass production process. Higher deposition rates result in thicker coatings on the substrate which correspond to improved energy attenuation properties for the coated article.

Conventional methods of producing organo indium chlorides generally involve either ligand exchange or alkylation of an indium compound to form the desired organo indium halide. The noted techniques require the use of solvents or pyrophoric compounds which result in additional processing or separation steps to obtain the desired organo indium chloride. Additionally, the known techniques for producing organo indium chlorides possess relatively long reaction times. *Gmelin Handbook of Inorganic and Organometallic Chemistry: In, Organoindium Compounds* 1, 8th Edition; Wolfgang Petz, Ed.; Springer-Verlag, Berlin: 1991.

organo indium chlorides are produced through alkylation of indium trichloride with an alkyl lithium compound. This is typically the most used procedure for generating organo indium chlorides. The reaction is generally carried out in a solvent of diethyl ether, benzene, or toluene for about 1 to 2 days under agitation. Upon completion of the reaction, the desired organo indium chloride is separated through sublimation.

An additional method of producing organo indium chlorides involves ligand exchange between indium trichloride and trialkyl indium, a pyrophoric compound. The reaction is carried out in ether, benzene, or toluene and provides quantitative yields in less than 6 hours.

Additionally, *Comprehensive Organometallic Chemistry*, eds. Geoffrey Wilkinson; F. Gordon A. Stone; Edward W. Abel, Pergamon Press, Oxford, 1982, vol. I, chp.7. discloses that indium metal, in general, reacts slowly with alkyl bromides or iodides. The reaction rate is enhanced when activated indium metal is utilized. The activation of the metal is accomplished by reacting indium trichloride with potassium in solution. The mixture is refluxed under nitrogen for four to six hours yielding a finely divided black metal powder. The powder reacts with the noted alkyl halide to form dialkyl indium bromide or iodide.

Thus, known methods of producing organo indium chlorides require alkylation or ligand exchange processes. The reactions are typically carried out in a solvent and therefore, require additional processing or separation steps to recover the desired organo indium chloride. The conventional methods also require extended reaction times. Activators may also be added to the indium metal to enhance the reaction process with halides. However, conventional indium activators involve compounds that result in additional processing steps to enhance the recovery of the desired organo metal halide.

It would be an advantage to produce an organo indium chloride directly from indium metal using an organo chloride as the organo group source. The direct synthesis of an organo indium chloride from indium metal would eliminate the use of pyrophoric compounds or the production of organo indium chlorides in a form that does not require additional solvents, processing, or separation techniques. Furthermore, it would be advantageous to develop a method with significantly reduced reaction times over those required with conventional organo indium chloride processes. The direct synthesis of organo indium chlorides from an indium metal melt would therefore improve the economics of producing the compounds over known processes.

It would also be advantageous to utilize an activator in the indium metal melt during the direct synthesis of organo indium chlorides. An activator would accelerate the reaction rate of the organo indium chloride from the indium melt.

It would be a further advantage to utilize an activator that would regenerate within the indium metal melt once the generation of organo indium chloride is initiated. The regeneration of an activator enhances the continuation of the reaction with the addition of fresh reactants, but without adding additional activators.

SUMMARY OF THE INVENTION

In accordance with the present invention, there is provided a novel method of producing organo indium chlorides by contacting an organo chloride directly with an indium metal melt. The organo chloride reacts with the indium metal melt to form an organo indium chloride in a form suitable for use as a precursor gas for chemical vapor deposition processes. The method results in the production of a diorgano indium chloride or organo indium dichloride.

The method of the present invention is carried out in a reaction vessel containing a metal melt. A vaporous organo source, such as methyl chloride, is injected into the indium metal melt wherein the components react to form an organo indium chloride. The resulting organo indium chloride compound is directed away from the reaction vessel and recovered. The type of organo indium chloride which results is dependent upon the contacting time of the organo chloride with the indium melt. For instance, lower contacting times will result in the formation of organo indium dichloride. Increased contacting times will produce diorgano indium chloride.

The reaction of the present inventive method is enhanced through the addition of an activator to the indium metal melt.

The activator increases the reaction rate of the organo chloride with the indium metal. Suitable activators include various halide and oxide compounds.

It is an object of the present invention to produce an organo indium chloride by contacting an organo chloride directly with an indium metal melt. The direct synthesis of organo indium chlorides from an indium melt enables the recovery of the desired compound without requiring the use of solvents during the reaction and without the need for additional separation steps in the process. Furthermore, the method of the present invention uses reaction components that are abundant and non-pyrophoric.

It is also an object of the present invention to provide a process for the direct synthesis of an organo indium chloride that possesses reduced reaction times over the known organo indium chloride formation processes. The duration of the reaction of the present inventive method is significantly reduced over the known prior art processes. The reduced reaction times enable the continuous production of organo indium chlorides.

It is a further object of the present invention to utilize an activator in the production of an organo indium chloride from an indium metal melt. An activator enhances the reaction rate of the indium metal with the organo chloride.

It is also an object of the present invention to utilize an activator that is regenerated in the indium melt. The regeneration of the activator facilitates the continuous production of the desired organo indium chloride at an enhanced rate by addition of the limiting reactant, indium metal, while continuously injecting the organo chloride into the melt.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which.

DETAILED DESCRIPTION OF THE PREFERRED EMBODIMENT

Figure 1:
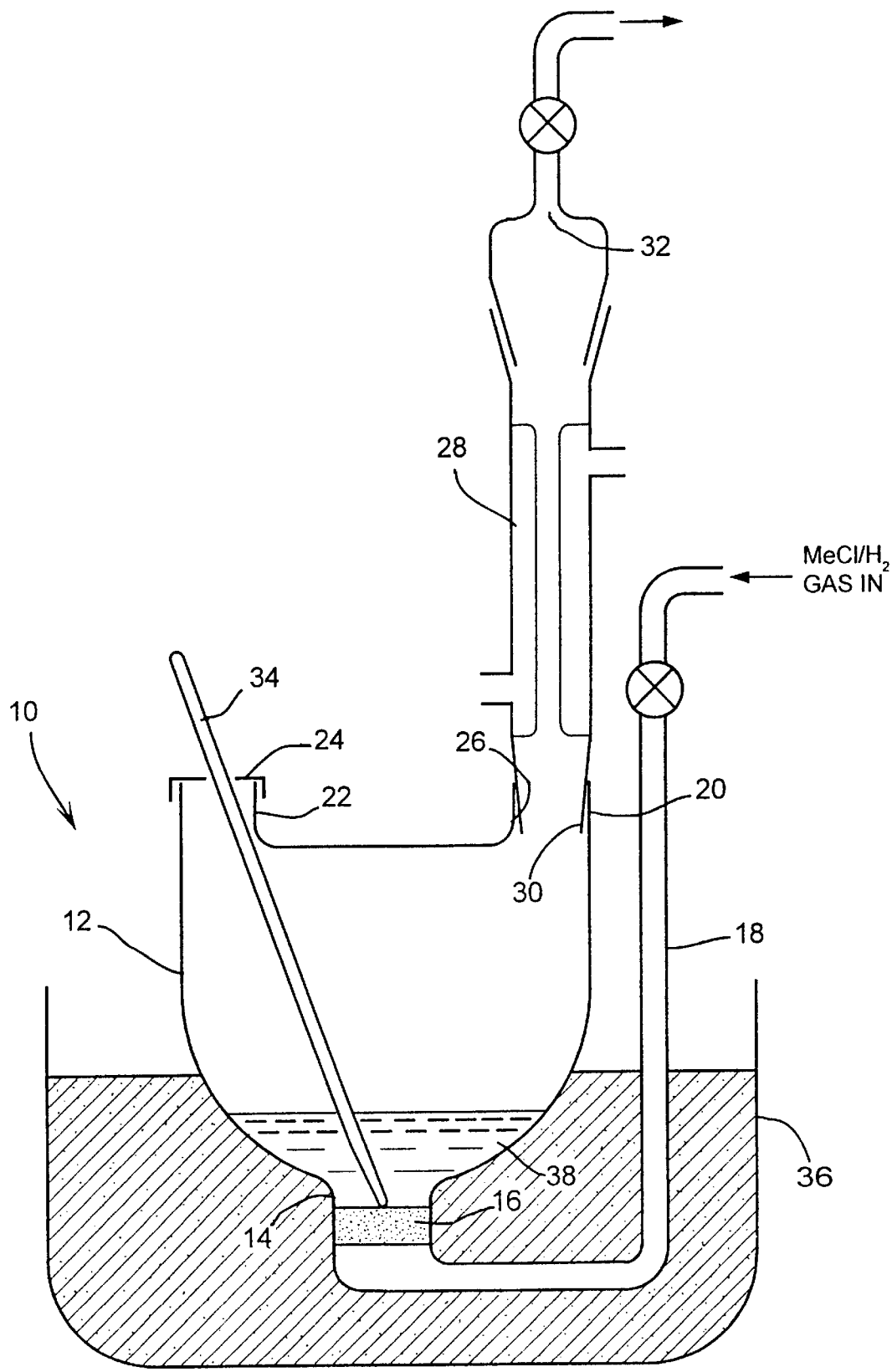
FIG. 1 is a schematic view of a laboratory apparatus suitable for demonstrating the method of the present invention in accordance with Examples I–IV and Predictive Example I.

In accordance with the method of the present invention, it has been discovered that organo indium chloride compounds may be formed directly from an indium metal melt by direct contact with an organo chloride. The method, in general, utilizes the flow of a vaporous organo chloride through an indium metal melt wherein the reaction between the components results in the formation of the desired organo indium chloride compound. The method is suitable for forming diorgano indium chloride or organo indium dichloride or mixtures thereof.

The method of the present invention is intended to utilize indium as the metal for formation of the melt. The organo indium chloride compounds produced from the inventive method provide a suitable metal source for forming indium oxide coatings. For example, indium is a desirable metal used in the formation of metal oxides on glass substrates because of the enhanced spectral, electrical, and energy attenuation properties it imparts to a coated article. However, gallium metal may be suitable for use with the present method for the formation of organo gallium chlorides.

The organo source utilized in the inventive method is generally an organo chloride. The preferred compound is methyl chloride for the formation of dimethyl indium chloride or methyl indium dichloride. Methyl chloride is provided as a vapor for use in the present method. The vaporous reactant is generally bubbled through the indium metal melt in the reaction vessel. Other organo chlorides that are more reactive toward indium metal are suitable for use with the present method to provide organo indium chloride compounds. For example, organo chlorides could include ethyl chloride, propyl chloride, neopentyl chloride, chloromethyltrimethylsilane, chlorotrifluoromethane, or chlorobenzene. Some of the organo chlorides may be liquids at room temperature. Thus, conventional vaporizing techniques may be utilized to place the organo chloride in the proper phase for use in the present inventive process.

Alternatively, the organo source may include other organo halides such as an organo bromide or iodide. Although the noted compounds may be more costly than the preferred organo chlorides, they are suitable for forming organo indium halides in accordance with the inventive method. The organo group in the organo halide compound may include groups similar to those previously disclosed for the organo chloride sources.

Additionally, hydrogen may be added to the organo chloride stream as a reducing agent. Hydrogen accelerates the reduction of both the indium and organo chloride, thus resulting in improved reaction rates. Hydrogen is present in the organo chloride at about 5 mole percent to about 60 mole percent. The preferred hydrogen content of the mixed organo chloride/hydrogen vapor stream is about 10 mole percent. The principal feature of the reducing agent is the reaction with an indium halide functional group in the melt in order to produce a volatile halide product and indium in a lower oxidation state. Thus, reducing agents stronger than hydrogen are suitable for use in the present inventive method. For example, trimethylsilane, dichlorosilane, ethylene, or acetylene may be used as reducing agents.

The reaction between the indium metal melt and the preferred methyl chloride results in the formation of either dimethyl indium chloride or methyl indium dichloride. The product formed is dependent upon the contacting time of the organo chloride with the indium metal. Shorter contacting times result in more methyl indium dichloride. Longer contacting time produces more of the dimethyl indium chloride. Thus, the reaction between the indium metal melt and methyl chloride is indicated as follows:

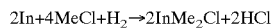
$$2In+4MeCl+H_2 \rightarrow 2InMe_2Cl+2HCl$$

Or

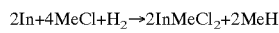
$$2In+4MeCl+H_2 \rightarrow 2InMeCl_2+2MeH$$

In accordance with the present invention, an activator is optionally included with the indium metal melt to enhance the reaction rate. The activator is melted with the metal to assist in initiating the reaction between the metal and the organo chloride. In general, the activator may include various halides or oxides. The halides can include $Cl_2$, HCl, $InCl_3$, $FeCl_3$, $(PtCl_4)^{2-}$, $PdCl_2$. The oxide activators include $In_2O_3$, $TiO_2$, $NiO2$, $Fe_2O_3$. The function of the activator is to react with the indium metal to generate a sub-valent reactive indium species. Thus, other metal halides or metal oxides that are capable of forming sub-valent indium species in the melt are suitable for use with the present invention.

In accordance with the present inventive method, the preferred activators are those which contain indium, such as $InCl_3$ or $In_2O_3$. The indium containing activators are preferred because they regenerate in the melt. Therefore, the continuous addition of an activator is not necessary once the melt is formed and the reaction is initiated.

The activators are melted directly with the indium metal at about 5 mole percent to about a 50 mole percent to form the melt. The preferred activator composition is about ten mole percent.

The inventor proposes the following theory regarding the chemical reaction that may take place. However, the inventor does not wish to limit the invention to just this possible explanation, and therefore offers it merely as an aid to understanding the results of the present inventive process.

During the heating of the indium metal and the activator, a melt is formed. The inventor proposes that, upon heating, the indium metal is reducing the halide or oxide compounds to generate sub-valent indium compounds ($In^I$ or $In^{II}$) as indicated by:

$$2In+InCl_3 \rightarrow 3\text{"InCl"}$$

The reaction is performed in excess indium and usually proceeds near the melting point of indium (159° C.). At this point, the inventor believes, a fairly facile reaction occurs between the $MeCl/H_2$ and the sub-valent indium compounds. The initial reaction is probably an oxidative addition of MeCl across an $In^I$ metal center to generate methyl indium dichloride, which undergoes a transformation to $[InMe2][InCl_4]$ as illustrated below:

$$\text{"InCl"}+MeCl \rightarrow InMe2Cl \leftrightarrow [InMe2][InCl_4]$$

Upon heating, the $[InMe2][InCl_4]$ complex may decompose to dimethyl indium chloride and $InCl_3$. The $InCl_3$ can then react with excess indium to reform the reactive sub-valent group, as indicated below:

$$[InMe2][InCl_4] \rightarrow InMe2Cl+InCl_3$$

$$2In+InCl_3 \rightarrow 3\text{"InCl"}$$

In operation, the method of the present invention is carried out in a conventional reaction vessel that permits the formation of the indium melt and the contacting of the organo chloride with the melt. The vaporous organo chloride is generally introduced at the bottom of the vessel and permitted to bubble through the melt in order for the reaction of the present invention to occur. However, other conventional means enabling vapor/liquid contact may be suitable for practicing the method of the present invention.

For the continuous production of organo indium chlorides, the vessel must also provide an appropriate means to withdraw the resulting organo indium chloride and thus permit the continuous production of the desired compound. The organo indium chloride is then recovered downstream from the vessel. Additionally, to permit continuous production the vessel must have an inlet means for the introduction of additional indium metal, which is the limiting reactant in the present inventive method.

The preferred method of the present invention is initiated in the reaction vessel wherein the indium and activator are heated to form a red indium metal melt. The red liquid generally is formed around 240° C. The melt is generally maintained during the reaction between about 240° C. to about 350° C., and preferably between about 280° C. and about 300° C.

Upon formation of the melt, the preferred methyl chloride, and optionally hydrogen, is bubbled through the melt wherein the reaction of the present invention takes place. The contacting time between the vapor and the melt impacts which form of organo indium chloride is produced. A methyl indium dichloride is evolved with contacting times no more than about 0.5 seconds. Longer contacting times in the range of about 10 seconds or greater produce the dimethyl indium chloride. Contacting times between the two ranges will result in a mixture of organo indium chloride compounds.

The recovery of the organo indium chloride is accomplished downstream of the reaction vessel. The organo indium chloride is preferably recovered in the vapor phase. However, system limitations involved in given recovery processes and equipment may result in the condensation and further solidification of the desired organo indium chloride compound. Conventional recovery equipment or vessels are suitable for practicing the present invention. Additionally, argon gas, or other inert gases, may be utilized to convey or sweep the desired organo indium chloride compounds into a recovery vessel.

Additionally, the recovery of the desired organo indium chlorides may be enhanced by the utilization of a polar aprotic solvent to place the organo indium chloride into solution. For instance, ethyl acetate may be utilized as a solvent to sweep solidified organo indium chlorides from the recovery vessel. Furthermore, polar aprotic solvents are suitable for conveying the organo indium chlorides to a vaporizer in a chemical vapor deposition process. Thus, the use of a polar aprotic solvent not only assists in the recovery and collection of the desired organo indium chlorides, but also places the material in a desirable form for use in a chemical vapor deposition process.

The organo indium chlorides resulting from the present inventive method are suitable for use as precursor gases for laying down indium oxide coatings, or doped indium oxide coatings, through conventional chemical vapor deposition processes. Moreover, the use of dimethyl indium chloride significantly increase the deposition rate of indium oxide coatings over other known indium precursor gases. For example, the use of dimethyl indium chloride results in deposition rates in the order of 800 Angstroms per second versus 20 Angstroms per second with other known indium precursor gases. In a float glass production process, the higher deposition rates result in thicker coatings on the substrate. The thicker coating corresponds to enhanced spectral, electrical, and energy attenuation properties for the coated article.

The following examples, which constitute the best mode presently contemplated by the inventor for practicing the present invention, are presented solely for the purpose of further illustrating and disclosing the present invention, and are not to be construed as a limitation on the invention:

EXAMPLE I

FIG. 1 depicts a 0.500 L round flask 12 which was utilized as a lab scale reaction vessel 10 in practicing the method of the present invention. The flask had a 2.5 cm diameter neck 14 at the bottom within which a 1 cm thick course sintered glass frit 16 was attached. The bottom necked portion 14 of the flask 12 was attached to a gas inlet tube 18. The flask 12 had two necked openings 20,22 on the upper portion. One necked opening 20 served as a gas outlet 26. The second opening 22 was covered with a rubber septum 24. Approximately 40 grams of indium metal and 3.5 grams indium trichloride were added to the reaction vessel 10 above the glass frit 16. The reaction vessel 10 was then fitted with a water cooled condenser 28 which had an inlet 30 and outlet 32 at opposing ends. The condenser 28 was connected to the gas outlet 26 of the reaction vessel 10. A thermometer 34 was passed through the rubber septum 24 and placed in contact with the frit 16. An oil bubbler (not shown) was attached to the gas outlet 32 on top of the condenser by tubing to detect the flow of vapor from the reaction vessel 10. Additionally, a bubbler (not shown) was attached to a gas supply at the gas inlet tube 18 at the bottom of the reaction vessel 10. The gas inlet tube 18 was utilized to deliver the organo chloride reactant to the reaction vessel 10.

The lower portion of the reaction vessel 10 was placed into a sand bath 36 such that the level of sand was approximately 5 cm above the glass frit 16. The sand bath temperature was controlled to maintain the desired melt temperatures. The indium metal and indium trichloride melt 38 was heated above the indium metal melting point to about 240° C. wherein a reaction between the indium and indium trichloride occurred to produce a red liquid. Methyl chloride and a separate mixture of 5% hydrogen in argon were brought into the reaction vessel 10 through the gas inlet tube 18. The methyl chloride vapor stream was first directed into the reaction vessel so that the gas very gently bubbled through the melt 38. An equivalent stream of 5% hydrogen in argon was then added to the methyl chloride vapor stream.

After approximately 5 minutes, white crystals began to grow on the cooler portions of the reaction vessel. The temperature of the melt was increased to about 290° C. wherein a white crystalline material formed very rapidly on the cooler portions of the reaction vessel. After 12 hours, the reaction vessel 10 was cooled to about 21° C. and then taken into a dry box. The product was removed by inverting the reaction vessel and scraping the material from the inner walls of the flask 12. Approximately 42 grams of dimethyl indium chloride were recovered from the reaction vessel. The product was confirmed as dimethyl indium chloride through proton NMR spectroscopy and by melting point comparisons to known samples.

EXAMPLE II

The same procedure as described in Example I was generally duplicated in this Example. The reaction vessel utilized in Example I contained some residual activated indium metal, as a solid, in the vessel. The reaction vessel was charged with an additional 40 grams indium metal. The indium metal was heated to 280° C. and then the combined methyl chloride, hydrogen, and argon vapor stream was bubbled through the melt. White crystalline dimethyl indium chloride was formed on the cooler portion of the reactor. Approximately 51 grams of dimethyl indium chloride was recovered from the reaction vessel. The composition was confirmed through proton NMR spectroscopy and through melting point comparison with a known dimethyl indium chloride sample.

EXAMPLE III

The same procedure described in Example I was carried out in this Example with the exception of the use of a reaction vessel with a larger neck 14 to support the use of a 7.7 cm diameter frit. Approximately 5 grams of indium metal and about 0.5 grams of indium trichloride were charged to the reaction vessel and heated. At about 300° C., a red melt formed that did not completely cover the frit. A vaporous stream of methyl chloride 5% hydrogen in argon were gently bubbled through the melt for 5 hours. The reactor was cooled and the white crystalline product was removed to afford 6.6 grams of methyl indium dichloride as confirmed with the same method described in Example I.

EXAMPLE IV

The same procedure as described in Example I was generally duplicated in the present Example. Twenty grams of indium metal was charged to the reaction vessel 10 and heated beyond its melting point. At about 300° C., chlorine gas was gently bubbled through the molten indium metal for approximately 5 minutes affording a red melt. Methyl chloride and 5% hydrogen in argon were bubbled through the melt for 6 hours. A white crystalline dimethyl indium chloride was formed in the reaction vessel. Approximately 26 grams of product was recovered from the reactor and confirmed as dimethyl indium chloride through spectroscopy and melting point comparison tests.

EXAMPLE V

Figure 2:
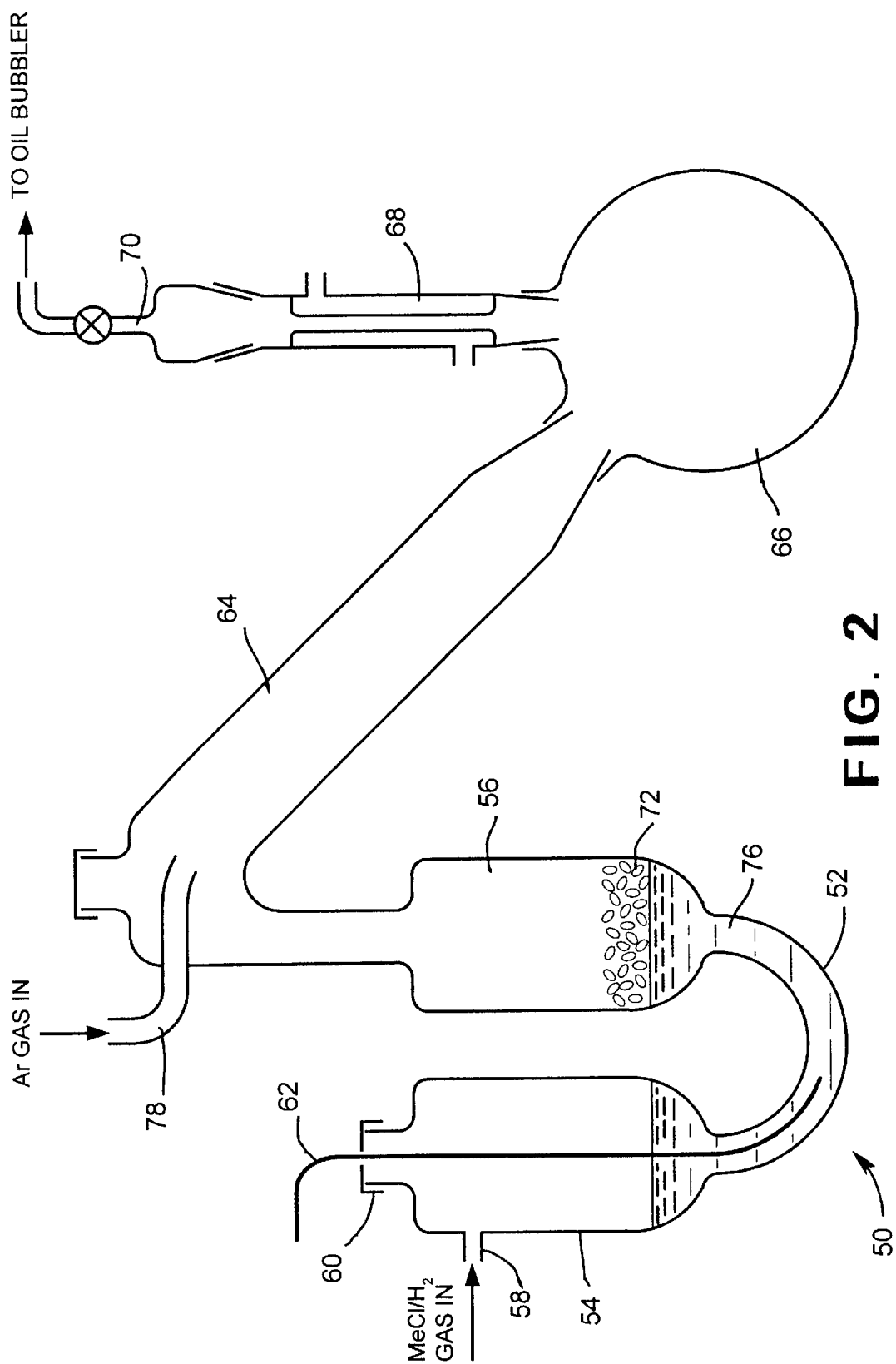
FIG. 2 is a schematic view of a laboratory apparatus suitable for use in practicing the present invention in accordance with Example V.

FIG. 2 depicts a lab scale reaction vessel 50 suitable for practicing the method of the present invention. The reaction vessel 50 included a U-tube 52, having a 10 mm inner diameter and about 7 cm in length. The U-tube 52 was utilized to connect two cylindrical vessels 54,56. Each of the cylindrical vessels 54,56 were 8 cm in height and 4 cm in diameter. One of the cylindrical vessels 54 had a gas inlet 58 connected to a gas supply (not shown). A septum 60 was placed over an opening in the cylindrical vessel 54 through which a thermocouple wire 62 was positioned to measure the temperature of the indium metal melt. The opposing cylindrical vessel 56 was fitted at the top with an outlet tube 64 having a 15 cm length and a 3 cm diameter. The outlet tube 64 was angled downward at an approximately 45° angle and connected to a 0.5 liter flask 66 at the opposing end. A condenser 68, having an outlet 70, was connected to the flask 66. The outlet 70 of the condenser 68 was connected to an oil bubbler (not shown).

Within an argon atmosphere dry box, a mixture of 10 grams of indium and 0.5 grams of indium trichloride were added to the reaction vessel 50. The cylindrical vessel 56 connected to the outlet tube 64 was filled with glass helices 72 (Scientific Glass, model number J-121, Helices 1/16 inch id), at approximately one-fourth of the volume of the vessel. The reaction vessel 50 and the outlet tube 64 were wrapped with heating tape (not shown) and brought to 290° C., resulting in the formation of a red indium melt 76.

Methyl chloride and a mixture of 5% hydrogen in argon were brought into the reaction vessel 50 through the gas inlet 58 so that the gas mixture gently bubbled through the indium melt 76. Within three minutes, a white crystalline product began to collect in the 0.5 flask 66. A slow stream of argon was passed through the outlet tube at a gas inlet 78 to assist the movement of white crystalline product to the 0.5 L flask. After 3.5 hours the gas mixture stopped bubbling through the indium melt due to the small amount remaining in the reactor. The reactor was cooled and then taken into an argon atmosphere dry box. The product was collected and tested with the same techniques indicated in Example I to afford 9.6 grams of dimethyl indium chloride.

PREDICTIVE EXAMPLE I

A 0.500 L round flask is utilized as a reaction vessel in practicing the method of the present invention. The reaction vessel is set up in accordance with Example I and as illustrated in FIG. 1. Approximately 40 grams of gallium metal and 3.5 grams of gallium trichloride are added to the flask above the glass frit. The reaction vessel is then fitted with a water cooled condenser which has an inlet and outlet at opposing ends. The condenser is connected to the gas outlet of the reaction vessel. A thermometer is passed through the rubber septum and placed in contact with the frit. An oil bubbler is attached to the gas outlet on top of the condenser to detect the flow of vapor from the reaction vessel. Additionally, a bubbler is attached to a gas supply at the gas inlet tube at the bottom of the reactor. The gas inlet tube is utilized to deliver the organo chloride reactant to the reaction vessel.

The lower portion of the reaction vessel is placed into a sand bath such that the level of sand is approximately 5 cm above the glass frit. The sand bath temperature is controlled to maintain the desired melt temperatures. The gallium metal and gallium trichloride mixture is heated above its melting point to about 240° C. wherein a reaction between the gallium and gallium trichloride occurs to produce a red liquid. Methyl chloride and a separate mixture of 5% hydrogen in argon are brought into the reaction vessel through the gas inlet tube. The methyl chloride vapor stream is first directed into the vessel so that the gas very gently bubbles through the indium melt. The stream of 5% hydrogen in argon is then added to the methyl chloride vapor stream.

After a short period of time, crystals should grow on the cooler portions of the reaction vessel. The temperature of the melt is then slightly increased so that the crystalline material forms rapidly on the cooler portions of the reaction vessel. The reaction vessel is then cooled and taken into a dry box to recover the crystalline dimethyl gallium chloride.

In accordance with the provisions of the patent statutes, the present invention has been described in what is considered to represent its preferred embodiment. However, it should be noted that the invention can be practiced otherwise than as specifically illustrated and described without departing from its spirit and scope.

What is claimed is:

1. A method of producing an organo indium chloride comprising contacting, in the absence of any solvent, an organo chloride with an indium metal melt to produce an organo indium chloride.

2. A method according to claim 1, wherein said organo chloride is included in a vaporous mixture of a reducing agent.

3. A method according to claim 2, wherein said reducing agent is hydrogen present in the vaporous mixture at about 5 mole percent to about 60 mole percent.

4. A method according to claim 1, wherein said resulting organo indium chloride is dimethyl indium chloride.

5. A method according to claim 1, wherein said resulting organo indium chloride is methyl indium dichloride.

6. A method according to claim 1, wherein said organo chloride is contacted with said indium melt at a contacting time of no more than about 0.5 seconds to produce methyl indium dichloride.

7. A method according to claim 1, wherein said organo chloride is contacted with said indium melt at a contacting time of no less than about 10 seconds to produce dimethyl indium chloride.

8. A method according to claim 1, wherein said contacting occurs at a temperature range of about 240° C. to about 350° C.

9. A method of producing an organo metal chloride wherein said metal is selected from the group consisting of indium or gallium, said method comprising contacting, in the absence of any solvent, an organo chloride with said metal to produce an organo indium chloride or an organo gallium chloride.

10. A method of producing an organo indium halide comprising contacting, in the absence of any solvent, an organo halide with an indium metal melt to produce an organo indium halide, said halide selected from the group consisting of chloride, iodide, or bromide.

11. A method of producing an organo indium chloride comprising:

(a) forming an indium metal melt at a temperature of about 240° C. to about 350° C.; and (b) contacting, in the absence of any solvent, an organo chloride with said indium metal melt to form an organo indium chloride.

12. A method according to claim 11, wherein said organo chloride is included in a vaporous mixture of a reducing agent.

13. A method according to claim 12, wherein said reducing agent is hydrogen present in the vaporous mixture at about 5 mole percent to about 60 mole percent.

14. A method according to claim 11, wherein said resulting organo indium chloride is dimethyl indium chloride.

15. A method according to claim 11, wherein said resulting organo indium chloride is methyl indium diachloride.

* * * * *